United States Patent
Chiang et al.

(10) Patent No.: US 11,452,681 B2
(45) Date of Patent: Sep. 27, 2022

(54) COSMETIC COMPOSITIONS TO PREVENT AND/OR AMELIORATE SKIN AGING AND METHODS OF APPLICATIONS

(71) Applicant: Orient EuroPharma Co., Ltd., Taipei (TW)

(72) Inventors: Chin-Chih Chiang, West Covina, CA (US); Mon-Jer Tsai, Taipei (TW)

(73) Assignee: ORIENT EUROPHARMA CO., LTD., Taipei (TW)

( * ) Notice: Subject to any disclaimer, the term of this patent is extended or adjusted under 35 U.S.C. 154(b) by 81 days.

(21) Appl. No.: 16/936,827

(22) Filed: Jul. 23, 2020

(65) Prior Publication Data

US 2021/0030655 A1 Feb. 4, 2021

Related U.S. Application Data

(60) Provisional application No. 62/879,617, filed on Jul. 29, 2019.

(51) Int. Cl.
| | | |
|---|---|---|
| *A61K 8/55* | (2006.01) | |
| *A61K 8/60* | (2006.01) | |
| *A61Q 19/08* | (2006.01) | |

(52) U.S. Cl.
CPC ............... *A61K 8/55* (2013.01); *A61K 8/602* (2013.01); *A61Q 19/08* (2013.01); *A61K 2800/59* (2013.01)

(58) Field of Classification Search
None
See application file for complete search history.

(56) References Cited

FOREIGN PATENT DOCUMENTS

| JP | 2008222643 A | * | 9/2008 | ............... A61K 8/55 |
| JP | 5737888 B2 | | 6/2015 | |
| WO | WO-2016091935 A1 | * | 6/2016 | ............. A61K 8/498 |

* cited by examiner

*Primary Examiner* — Nannette Holloman
(74) *Attorney, Agent, or Firm* — WPAT, PC

(57) ABSTRACT

A cosmetic composition to prevent and/or ameliorate skin aging and applications thereof are provided in the present disclosure and the cosmetic composition comprises cyclic phosphatidic acid and citrus flavonoids which is hesperidin and/or hesperetin wherein the preventing and/or ameliorating skin aging include, without limitation, promoting moisture retention of stratum corneum, promoting skin elasticity, increasing presence or elasticity of collagens and elastins in fibroblasts, increasing transfers of fibroblasts, promoting anti-oxidation, increasing generation of hyaluronic acid, alleviating wrinkles and skin textures, moderating melanin, reducing skin oil and preventing transepidermal water losses.

12 Claims, 8 Drawing Sheets

(8 of 8 Drawing Sheet(s) Filed in Color)

Score 3

Score 5

Score 7

Baseline: Score 3

Week 12: Score 7

Score 3

Score 5

Score 7

Baseline: Score 5

Week 12: Score 7

Score 3

Score 5

Score 7

Baseline: Score 3

Week 12: Score 7

Baseline Week 12

Baseline Week 12

Baseline　　　　　　Week 12

Baseline　　　　　　Week 12

COSMETIC COMPOSITIONS TO PREVENT AND/OR AMELIORATE SKIN AGING AND METHODS OF APPLICATIONS

CROSS REFERENCE TO RELATED APPLICATION

This application claims the benefit of the Provisional Application Ser. No. 62/879,617, filed on Jul. 29, 2019 by the present inventor.

BACKGROUND OF THE INVENTION

1. Field of the Invention

The present disclosure relates to a cosmetic product, particularly a cosmetic composition, for preventing and/or ameliorating skin aging and other applications thereof that are explained hereinafter.

2. Description of the Prior Art

Skin aging symptoms, such as wrinkles, sagging skin, pigmentation, skin darkening or dehydration, have a negative effect on a person's appearance. For that matter, sagging skin or wrinkles are attributed to dry stratum corneum or ultraviolet irradiation depleting essential ingredients of outer skin. The problems, for example, oily skin, dry skin, red/swollen skin, itchy skin, coarse pores, acnes, skin darkening or pigmentation, are common in skin that is not moisturized or is dehydrated. Moreover, the water content in a dehydrated person's skin, particularly the stratum corneum, will be reduced causing discomforts including dry skin, fine line, skin laceration, fast skin aging, dermatitis, itchy skin, cutaneous pain and burning skin. Skin darkening or pigmentation as the factor of a skin tone is related to melanin, which is the key factor to determine the skin color as it changes in heme and carotene in blood.

Currently, most anti-aging cosmetics for skin are designed to protect skin by counteracting free radicals or by eliminating or reducing irradiation-induced skin injuries. Among various antioxidants, superoxide dismutase (SOD) and coenzyme Q10 have been incorporated in cosmetic products widely to prevent skin aging. In addition, as disclosed in Japanese Patent JP5737888B2, cyclic phosphatidic acid is used in treatment of atopic dermatitis and sodium cyclic lysophosphatidic acid (NcPA) proves effectiveness in counteracting skin aging. However, how to deliver NcPA into the bottom layer of skin safely and effectively for the effect of preventing skin aging becomes a critical issue deserving to be studied by the persons skilled in the art.

Hesperidin and Hesperetin, both of which are categorized as flavonoid, are known for their antioxidant activity. However, there has been no study or report on penetrations of these ingredients into different skin layers and effects on skins. Accordingly, it is desired to understand the mechanisms of hesperidin or hesperetin delivered to skin layers and their effects on a human body.

As mentioned previously, it is desired to find a method to deliver ingredients with the anti-aging activity into skin layers and still keep these ingredients ameliorate skin aging; moreover, the effects of NcPA with citrus flavonoid incorporated on counteracting skin aging as well as their clinic efficiency are explained hereinafter.

SUMMARY OF THE INVENTION

The present disclosure aims to offer a cosmetic composition for preventing and/or ameliorating skin aging wherein the cosmetic composition proves effective in alleviation of skin aging that is evaluated and verified in a clinic trial.

The cosmetic composition for preventing and/or ameliorating skin aging comprises cyclic phosphatidic acid and citrus flavonoid wherein the citrus flavonoid is hesperidin and/or hesperetin.

The cyclic phosphatidic acid is represented by the structural formula (I):

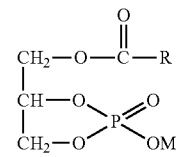

where R is linoleic acid, palmitic acid or oleic acid;
M is sodium (Na) or hydrogen (H); and
the molecular weight of sodium cyclic phosphoric ranges from 300 to 500.

The cyclic phosphatidic acid is sodium cyclic lysophosphatidic acid (NcPA).

The present disclosure further offers an application of the cosmetic composition with cyclic phosphatidic acid and citrus flavonoid mentioned previously and the application is about preparation of a cosmetic composition to prevent and/or ameliorate skin aging.

The cosmetic composition features the cyclic phosphatidic acid with the weight percentage between 0.01% and 0.5%.

The cosmetic composition features the citrus flavonoid with the weight percentage between 0.01% and 0.5%.

The cosmetic composition can be an ointment, a lotion, a cream, a gel, liquid drops, a spray, a solution, a face mask or an agent acceptable in pharmacy or cosmetology.

The cosmetic composition may comprise moisturizing agents, surfactants, UV absorbents, fragrances, anti-oxidants, preservatives, body pigments, color pigments, pH adjusting agents, solvents or any other ingredients for general cosmetics or topical dermatologic drug compositions.

The present disclosure further offers a method to prevent and/or ameliorate skin aging in which the cosmetic composition is applied on skin to be absorbed transdermally or on local skin topically at room temperature wherein the cosmetic composition comprises cyclic phosphatidic acid as well as citrus flavonoid that can be hesperidin and/or hesperetin.

The skin includes normal skin and aged skin.

The skin aging is a combination of wrinkles, fine lines, skin darkening, dehydration, absence of pigments and absence of skin elasticity.

The preventing and/or ameliorating skin aging include, without limitation, promoting moisture retention of stratum corneum, promoting skin elasticity, increasing presence or elasticity of collagens and elastins in fibroblasts, increasing transfers of fibroblasts, promoting anti-oxidation, increasing generation of hyaluronic acids, alleviating wrinkles and skin textures, moderating melanin, reducing skin oil and preventing transepidermal water losses.

In some embodiments, the present disclosure offers weight percentages of ingredients in the cosmetic composition comprising hesperidin and NcPA (or hesperetin and NcPA), both of which permeate skin and prove effectiveness in transdermal absorption for ameliorating skin aging, as shown in the in-vitro skin permeation test.

In some embodiments, the cosmetic composition proves effectiveness in preventing and/or ameliorating skin aging without side effects, as shown in the human clinic trial; the cosmetic composition with potentials in medical treatment and cosmetic medicine for ameliorating skin aging is known for the industrial application value.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
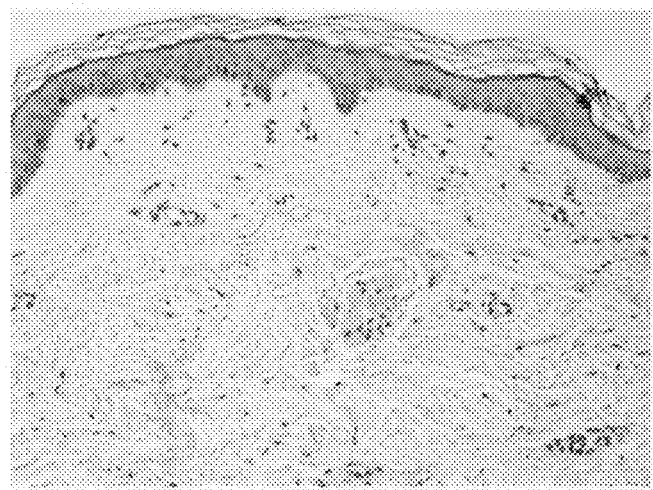
FIG. 1 demonstrates the reference standard of the hyaluronic acid score for Score 3, Score 5 and Score 7 in Embodiment 11.
Figure 1:
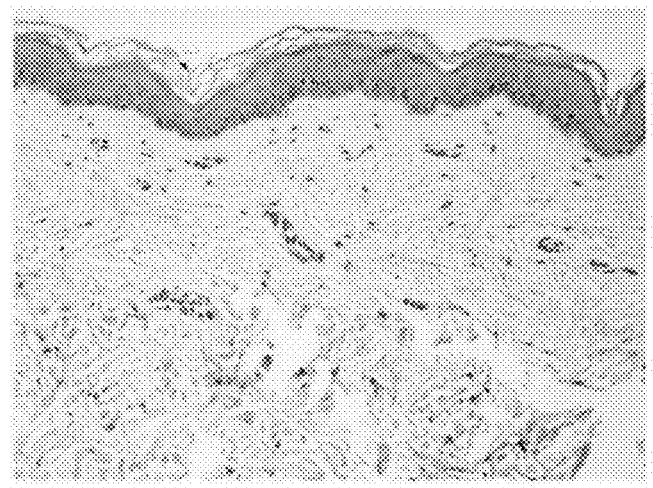
Figure 1:
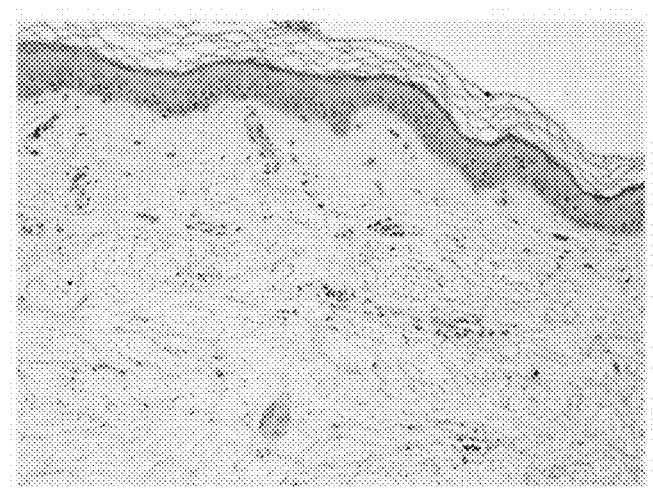

Unless otherwise stated, all technical and scientific terms in the present application, including the specification and claims, have definitions known to the persons who are skilled and have general knowledge in the art.

A cosmetic composition for preventing and/or ameliorating skin aging for skin care in the present disclosure is characteristic of a dosage form, which is adjusted flexibly and not specified, and particularly a formulation topically applied on skin.

As a topical product for skin, the cosmetic composition in the present disclosure could be made as a cosmetic, a medicine or a topical drug. Furthermore, a cosmetic composition features the dosage form including, without limitation, a solution, a lotion, a cream, a cleanser, a gel, an ointment or a paste.

In addition to primary ingredients, the cosmetic composition for the topical application in the present disclosure may comprise moisturizing agents, surfactants, UV absorbents, fragrances, anti-oxidants, preservatives, body pigments, color pigments, pH adjusting agents, solvents or any other acceptable ingredients for general cosmetics or topical dermatologic drug compositions, all of which have no negative effect on the scope of the present application.

In the cosmetic composition, an agent acceptable in pharmacy or cosmetology may comprise one or more reagents selected from a solvent, an emulsifier, a suspending agent, a decomposer, a binding agent, an excipient, a stabilizing agent, a chelating agent, a diluent, a gelling agent, a preservative, a lubricant, a surfactant and other similar agents or agents applicable to the cosmetic composition.

In the present disclosure, the cosmetic composition for preventing and/or ameliorating skin aging comprises cyclic phosphatidic acid and citrus flavonoid wherein the citrus flavonoid is hesperidin and/or hesperetin.

The cyclic phosphatidic acid is represented by the structural formula (I):

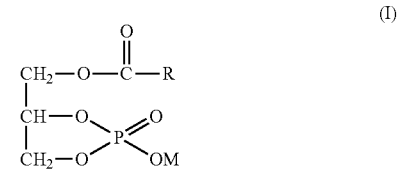

(I)

where R is linoleic acid, palmitic acid or oleic acid, M is sodium (Na) or hydrogen (H), and the molecular weight of sodium cyclic phosphoric ranges from 300 to 500.

In embodiments of the present disclosure, the cyclic phosphatidic acid is sodium cyclic lysophosphatidic acid (NcPA).

In the present disclosure, hesperidin is a natural glucoside existing in citrus and can be transferred to hesperetin after acidification based on a chemical reaction as follows:

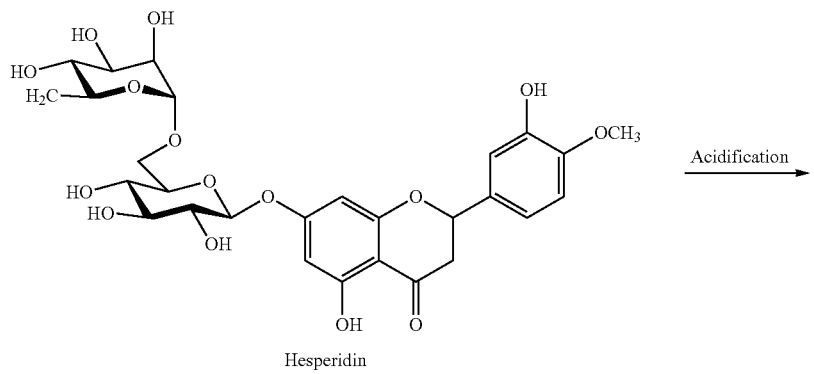

Hesperidin

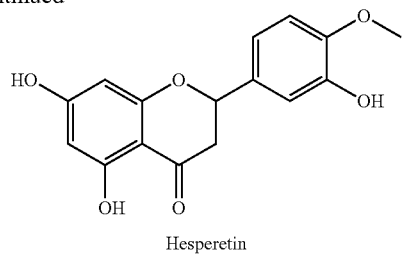

Hesperetin

The cosmetic composition for preventing and/or ameliorating skin aging is demonstrated in embodiments hereinafter that do not limit the scope of the cosmetic composition. The medicines or biological materials used hereinafter are available in the market and indicated in the following embodiments.

Embodiment 1: Ingredients and the Manufacturing Process of a Lotion with Cyclic Phosphatidic Acid and Hesperidin Ingredients and weight percentages of ingredients in a lotion with cyclic phosphatidic acid and hesperidin are shown in Table 1.

| Ingredient | Weight Percentage |
|---|---|
| Water | >80% |
| Propylene Glycol | 1-10% |
| Glycerin | 1-10% |
| Bis-Ethoxydiglycol Cyclohexane 1,4-Dicarboxylate | 1-10% |
| Sorbitol | <1% |
| Betaine | <1% |
| PEG-60 Hydrogenated Castor Oil | <1% |
| Carbomer | <1% |
| Triethylhexanol | <1% |
| Phenyl Trimethicone | <1% |
| Potassium Hydroxide | <1% |
| Polyglyceryl-10 Myristate | <1% |
| Hesperidin | <1% |
| Sodium Cyclic Lysophosphatidic Acid (NcPA) | <1% |
| Phenoxyethanol | <1% |
| Methylparaben | <1% |

In Table 1, the preferred contents of hesperidin and cyclic phosphatidic acid are 0.01-0.5 wt % and 0.01-0.5 wt %, respectively.

The manufacturing process of the lotion is shown as follows:

Oil phase: Bis-ethoxydiglycol cyclohexane 1,4-dicarboxylate, PEG-60 hydrogenated castor oil, triethylhexanol, phenyl trimethicone, polyglyceryl-10 myristate, phenoxyethanol and methylparaben are added into Container A in which temperature is heated to 70° C. and the mixture is stirred well.

Aqueous phase: Carbomer is slowly added into Container B with water inside, stirred and dissolved in water. Propylene Glycol, glycerin and sorbitol are sequentially added into Container B in which mixtures are stirred well and potassium hydroxide is further added for better consistency. Container B is heated to 70° C. at which mixtures are stirred continuously and phenoxyethanol as well as methylparaben are further added for stirring well.

Oil-water mixture: The mixture in Container A is added into Container B in which a new mixture is stirred well at 70° C. and then temperature is lowered to 50° C.

Lotion: Hesperidin and sodium cyclic lysophosphatidic acid (NcPA) are added into Container B in turn; the mixture in Container B is stirred well for production of the lotion.

Embodiment 2: Ingredients and the Manufacturing Process of a Lotion with Cyclic Phosphatidic Acid and Hesperetin Ingredients and weight percentages of ingredients in a lotion with cyclic phosphatidic acid and hesperetin are shown in Table 2.

TABLE 2

| Ingredient | Weight Percentage |
|---|---|
| Water | >80% |
| Propylene Glycol | 1-10% |
| Glycerin | 1-10% |
| Bis-Ethoxydiglycol Cyclohexane 1,4-Dicarboxylate | 1-10% |
| Sorbitol | <1% |
| Betaine | <1% |
| PEG-60 Hydrogenated Castor Oil | <1% |
| Carbomer | <1% |
| Triethylhexanol | <1% |
| Phenyl Trimethicone | <1% |
| Potassium Hydroxide | <1% |
| Polyglyceryl-10 Myristate | <1% |
| Hesperetin | <1% |
| Sodium Cyclic Lysophosphatidic Acid (NcPA) | <1% |
| Phenoxyethanol | <1% |
| Methylparaben | <1% |

In Table 2, the preferred contents of hesperetin and cyclic phosphatidic acid are 0.01-0.5 wt % and 0.01-0.5 wt %, respectively.

The manufacturing process of the lotion is shown as follows:

Oil phase: Bis-ethoxydiglycol cyclohexane 1,4-dicarboxylate, PEG-60 hydrogenated castor oil, triethylhexanol, phenyl trimethicone, polyglyceryl-10 myristate, phenoxyethanol and methylparaben are added into Container A in which temperature is heated to 70° C. and the mixture is stirred well.

Aqueous phase: Carbomer is slowly added into Container B with water inside, stirred and dissolved in water. Propylene glycol, glycerin and sorbitol are sequentially added into Container B in which the mixture is stirred well and potassium hydroxide is further added for better consistency. Container B is heated to 70° C. at which the mixture is stirred continuously and phenoxyethanol as well as methylparaben are further added for stirring well.

Oil-water mixture: The mixture in Container A is added into Container B in which a new mixture is stirred well at 70° C. and then temperature is lowered to 50° C.

Lotion: Hesperidin and sodium cyclic lysophosphatidic acid (NcPA) are added into Container B in turn; the mixture in Container B is stirred well for production of the lotion.

Embodiment 3: Ingredients and the Manufacturing Process of an Essence with Cyclic Phosphatidic Acid and Hesperidin Ingredients and weight percentages of ingredients in an essence with cyclic phosphatidic acid and hesperidin are shown in Table 3.

TABLE 3

| Ingredient | Weight Percentage |
|---|---|
| Water | >75% |
| Butylene Glycol | 5-15% |
| Glycerin | 5-15% |
| Hydrogenated Lecithin | <1% |
| Bis-Ethoxydiglycol Cyclohexane 1,4-Dicarboxylate | <1% |
| Phenoxyethanol | <1% |
| Carbomer | <1% |
| Cholesterol | <1% |
| Methylparaben | <1% |
| Hesperidin | <1% |
| Sodium Cyclic Lysophosphatidic Acid (NcPA) | <1% |
| Sodium Hydroxide | <1% |
| Xanthan Gum | <1% |
| Dipotassium Glycyrrhizate | <1% |
| Hydrogenated Lysolecithin | <1% |

In Table 3, the preferred contents of hesperidin and cyclic phosphatidic acid are 0.01-0.5 wt % and 0.01-0.5 wt %, respectively.

The manufacturing process of the essence is shown as follows:

Oil phase: Glycerin, hydrogenated lecithin, bis-ethoxydiglycol cyclohexane 1,4-dicarboxylate, phenoxyethanol and hydrogenated lysolecithin are added into Container A at room temperature at which the mixture is stirred well; cholesterol, methylparaben and hesperidin are added into Container A in turn and dissolved in the mixture therein.

Aqueous phase: Carbomer is slowly added into Container B with water inside, stirred and dissolved in water.

Essence: The mixture in Container A is added into Container B in which a new mixture is stirred well; sodium hydroxide is slowly added into Container B for a pH value adjustment.

Embodiment 4: Ingredients and the Manufacturing Process of an Essence with Cyclic Phosphatidic Acid and Hesperetin Ingredients and weight percentages of ingredients in an essence with cyclic phosphatidic acid and hesperetin are shown in Table 4.

TABLE 4

| Ingredient | Weight Percentage |
|---|---|
| Water | >75% |
| Butylene Glycol | 5-15% |
| Glycerin | 5-15% |
| Hydrogenated Lecithin | <1% |
| Bis-Ethoxydiglycol Cyclohexane 1,4-Dicarboxylate | <1% |
| Phenoxyethanol | <1% |
| Carbomer | <1% |
| Cholesterol | <1% |
| Methylparaben | <1% |
| Hesperetin | <1% |
| Sodium Cyclic Lysophosphatidic Acid (NcPA) | <1% |
| Sodium Hydroxide | <1% |
| Xanthan Gum | <1% |
| Dipotassium Glycyrrhizate | <1% |
| Hydrogenated Lysolecithin | <1% |

In Table 4, the preferred contents of hesperetin and cyclic phosphatidic acid are 0.01-0.5 wt % and 0.01-0.5 wt %, respectively.

The manufacturing process of the essence is shown as follows:

Oil phase: Glycerin, hydrogenated lecithin, bis-ethoxydiglycol cyclohexane 1,4-dicarboxylate, phenoxyethanol and hydrogenated lysolecithin are added into Container A at room temperature at which the mixture is stirred well; cholesterol, methylparaben and hesperidin are further added into Container A.

Aqueous phase: Carbomer is slowly added into Container B with water inside, stirred and dissolved in water.

Essence: The mixture in Container A is added into Container B in which a new mixture is stirred well; sodium hydroxide is slowly added into Container B for a pH value adjustment.

Embodiment 5: In-Vitro Skin Permeability Test Based on Formula Product with Hesperidin or Hesperetin A series of cosmetics prepared with hesperidin or hesperetin, for example, lotions and essences, are tested by in-vitro skin permeation to investigate the percutaneous absorptions of cosmetics.

Conditions for the in-vitro skin permeation test:

Skin Specimen: Human cadaver skin;

Apparatus for the skin permeation test: Horizontal skin permeation device;

Area of skin effectively permeated: 0.64 cm$^2$;

Acceptor vehicle: 3.5 mL water solutions with 10% PEG 400 dissolved in water;

Temperature: 32° C.;

Test time: 24 hours;

Number of trials: Each specimen tested three times.

The steps of the skin permeation test are shown as follows:

1. Human cadaver skin is placed on a horizontal skin permeation device in which 10% PEG 400 solution is used as the receptor vehicle, at 32° C.; a formula product is applied on the skin surface in triplicate.
2. Study period: The test is terminated after 24 hours; specimens are collected from the receptor vehicle.
3. Processing of residues on outer layer skin: After termination of the test, skin on which a formula product is applied on is removed from the horizontal skin permeation device and laid on a slab. A piece of Scotch tape (size: 1×3 cm$^2$) is placed on the skin surface and a gentle pressure is applied to the tape to strip the surface skin layer. Note: The practice is repeated for a total of five times to remove any possible cosmetic residue left on skin surface. The residues on the tape are not analyzed.

4. Specimens on epidermis: After the process in step 3, the same practice as described in Step 3 is repeated 15 times each with a piece of Scotch tape (size: 1×3 cm$^2$). Note: Each piece of tape after skin stripping is collected together in a 20 mL scintillation vial for extraction of cosmetic ingredients using methanol as a solvent.

5. Specimens on dermis: Skin after the process in step 4 is cut into pieces with a scissors. The pieces are collected into a 20 mL scintillation vial. Methanol is added into the vial to extract the cosmetic ingredients by using a homogenizer.

6. Specimens processed from step 4 to step 5 are analyzed for the content of hesperidin or hesperetin using HPLC.

Conditions of HPLC:
Equipment: Waters, Photodiode Array Detector equipped with an autosampler
Column: C18, 5 μm; 4.6×250 mm
Temperature: 45±5° C.
Mobile phase: 0.2% acetic acid (pH=3):methanol=70:30 by volume
Flow velocity: 1.0 mL/min Test results for formula products with hesperidin are shown in Table 5:

TABLE 5

| Formula product | Lot Number | Content of hesperidin | | |
|---|---|---|---|---|
| | | Epidermis (μg/g) | Dermis (μg/g) | Skin permeation of hesperidin (μg/cm$^2$/24 hrs) |
| Hydrating lotion | P28736-02 | 1,462 | 8 | 0.16 |
| Hydrating night cream | P29422-01 | 0 | 0 | 0 |

A hydrating lotion and a hydrating night cream, each of which is prepared with hesperidin mixed, are produced for studying skin permeation of hesperidin according to the content of hesperidin on each skin specimen processed in previous steps.

As shown in Table 5, the test results are summarized as follows: (a) hydrating lotion: the contents of hesperidin in a hydrating lotion on 1 g epidermis and 1 g dermis are 1.4 mg and 8 μg, respectively; skin permeation of hesperidin permeating through skin and assayed in the receptor vehicle is 0.16 μg/cm$^2$/24 hrs; (b) hydrating night cream: no hesperidin is detected in the receptor vehicle meaning no hesperidin in a hydrating night cream deposits on epidermis or dermis.

Test results for formula products with hesperetin are shown in Table 6:

TABLE 6

| Formula product | Lot Number | Content of hesperetin | | |
|---|---|---|---|---|
| | | Epidermis (μg/g) | Dermis (μg/g) | Skin permeation of hesperetin (μg/cm$^2$/24 hrs) |
| Anti-aging lotion | P29433-01 | 14 | 14 | 1.73 |
| Anti-aging essence | P29429-01 | 26 | 131 | 2.35 |
| Anti-aging cream | P29431-01 | 1 | 1 | 0 |

An anti-aging lotion, an anti-aging essence and an anti-aging cream, each of which is prepared with hesperetin mixed, are produced for studying skin permeation of hesperetin according to the content of hesperetin on each skin specimen processed in previous steps.

As shown in Table 6, the test results are summarized as follows: (a) anti-aging lotion: the contents of hesperetin in an anti-aging lotion on 1 g epidermis and 1 g dermis are 14 μg and 14 μg, respectively; skin permeation of hesperetin permeating through skin and assayed in the receptor vehicle is 1.73 μg/cm$^2$/24 hrs; (b) anti-aging essence: the contents of hesperetin in an anti-aging essence on 1 g epidermis and 1 g dermis are 26 μg and 131 μg, respectively; skin permeation of hesperetin permeating through skin and assayed in the receptor vehicle is 2.35 μg/cm$^2$/24 hrs; (c) anti-aging cream: the contents of hesperetin in an anti-aging cream on 1 g epidermis and dermis are 1 μg and 1 μg, respectively; no hesperetin is detected in the receptor vehicle meaning no hesperetin in an anti-aging cream deposits on epidermis or dermis.

It can be seen from test results that hesperidin or hesperetin mixed in a cosmetic is transmitted to epidermis and dermis. For example, 0.1 mg-5 mg hesperidin and 1 μg-50 μg hesperidin are absorbed by 1 g epidermis and 1 g dermis, respectively; 0.1 μg-50 μg hesperetin and 0.1 μg-10 μg hesperetin are absorbed by 1 g epidermis and 1 g dermis, respectively. Among these cosmetics, the anti-aging essence, lot number P29429-01, with ingredients of hesperetin (0.01-0.5 wt %) and NcPA (0.01-0.5 wt %) presents better skin permeation and is selected as a test object of a clinic trial for the effect of preventing skin aging.

Embodiment 6: Human Clinic Trial Based on the Anti-Aging Essence with Cyclic Phosphatidic Acid and Hesperetin In this embodiment, the effect of a cosmetic composition with cyclic phosphatidic acid and hesperetin on prevention and/or alleviation of skin aging is tested in a human clinic trial through a formula product, lot number P29429-01, for its effect and safety.

The formula product is the anti-aging essence, lot number P29429-01, in which hesperetin (0.01-0.5 wt %) and NcPA (0.01-0.5 wt %) are mixed.

Clinic trial Protocol: 35 subjects aged from 40 to 65 years old with facial skin aging were treated with the formula P29429-01 for 12 weeks, and the effects on skin status were tested to evaluate the efficacy. 12 of the subjects were additionally received an adjunct study of skin tissue sections. The dosage of the formula P29429-01 is about a finger pulp (approximately 0.5 c.c.) and was applied once in the morning and at night.

Embodiment 7: Promotion of the Water Content in Stratum Corneum and Skin Elasticity In Embodiment 7, any changes in the water content of facial skin (the skin elasticity) in Week 4 and Week 12 relative to the baseline (data collected one week before the human clinic trial) are evaluated and taken as the major indicator of the curative effect.

The statistics for the water content of subjects' facial skin are shown in Table 7.

TABLE 7

| Time | N | Mean | S.D. | Min. | Max. |
|---|---|---|---|---|---|
| Baseline | 35 | 61.9 | 15.19 | 24.5 | 84.2 |
| Week 4 | 35 | 67.0 | 13.72 | 38.7 | 97.6 |
| Week12 | 35 | 67.6* | 12.17 | 38.5 | 88.2 |

Asterisk (*) means a significant difference between the statistic in Week 4 (or Week 12) and the baseline (* $p < 0.05$;  $p < 0.01$; * $p < 0.001$)

As shown in Table 7 for the comparison between the test data for the water content of subjects' skin and the baseline, the promotion in Week 12 indicates the statistically significant effect (the mean in Week 12, 67.60 (±12.17), relative to the baseline, 61.86 (±15.19); p=0.0148), that is, the water content of stratum corneum increases significantly. Moreover, the water content of subjects' stratum corneum in Week 4 also increases (mean=67.00 (±13.72)) and moisture retention of subjects' stratum corneum in Week 4 increase by 10% stably.

The statistics for skin elasticity of subjects' facial skin are shown in Table 8.

TABLE 8

| Time | N | Mean | S.D. | Min. | Max. |
|---|---|---|---|---|---|
| Baseline | 35 | 0.66 | 0.08 | 0.467 | 0.857 |
| Week 4 | 35 | 0.71 | 0.07 | 0.58 | 0.879 |
| Week12 | 35 | 0.73*** | 0.1 | 0.543 | 1 |

Asterisk (*) means a significant difference between the statistic in Week 4 (or Week 12) and the baseline (* $p < 0.05$;  $p < 0.01$; * $p < 0.001$)

As shown in Table 8 for the comparison between the test data for skin elasticity of subjects' skin and the baseline, the promotion in Week 12 indicates the statistically significant effect (the mean in Week 12, 0.73 (±0.1), relative to the baseline, 0.66 (±0.08); p<0.0001), that is, skin elasticity increases by 10% in Week 12. Accordingly, the cosmetic composition in the present disclosure proves effectiveness in the better water content of skin and skin elasticity.

Embodiment 8: Improvement of Melanin

In Embodiment 8, any changes in melanin on subjects' faces in Week 4 and Week 12 relative to the baseline (data collected one week before the human clinic trial) are evaluated and taken as the major indicator of the curative effect.

The statistics for melanin on subjects' facial skin are shown in Table 9.

TABLE 9

| Time | N | Mean | S.D. | Min. | Max. |
|---|---|---|---|---|---|
| Baseline | 35 | 185.03 | 31.23 | 136 | 258 |
| Week 4 | 35 | 182.74 | 29.0 | 129 | 258 |
| Week12 | 35 | 190.29 | 38.66 | 125 | 290 |

As shown in Table 9 for the comparison between the test data for melanin on subjects' facial skin and the baseline, melanin on subjects' facial skin in Week 12 is improved by 3% (from the baseline (185.03 (±31.23)) to the mean in Week 12 (190.29 (±38.66))). Accordingly, the cosmetic composition in the present disclosure proves effectiveness in improvement of melanin.

Embodiment 9: Alleviation of Skin Oil

In Embodiment 9, any changes in skin oil on subjects' faces in Week 4 and Week 12 relative to the baseline (data collected one week before the human clinic trial) are evaluated and taken as the major indicator of the curative effect.

The statistics for skin oil on subjects' facial skin are shown in Table 10.

TABLE 10

| Time | N | Mean | S.D. | Min. | Max. |
|---|---|---|---|---|---|
| Baseline | 35 | 47.29 | 35.42 | 5 | 133 |
| Week 4 | 35 | 44.51 | 32.28 | 3 | 143 |
| Week12 | 35 | 41.8 | 32.41 | 3 | 154 |

As shown in Table 10 for the comparison between the test data for skin oil on subjects' facial skin and the baseline, skin oil on subjects' facial skin in Week 12 decreases by 11% (from the baseline (47.29 (±35.42)) to the mean in Week 12 (41.8 (±32.41)). Accordingly, the cosmetic composition in the present disclosure proves effectiveness in alleviating skin oil.

Embodiment 10: Alleviation of Transepidermal Water Losses

In Embodiment 10, any changes in transepidermal water losses (TEWL) from subjects' skin in Week 4 and Week 12 relative to the baseline (data collected one week before the human clinic trial) are evaluated and taken as the major indicator of the curative effect.

TABLE 11

| Time | N | Mean | S.D. | Min. | Max. |
|---|---|---|---|---|---|
| Baseline | 35 | 13.55 | 17.45 | −29.7 | 99.9 |
| Week 4 | 35 | 10.99 | 5.69 | 4.0 | 28.6 |
| Week12 | 35 | 11.18 | 5.87 | 2.7 | 31.8 |

As shown in Table 11 for the comparison between the test data for transepidermal water losses of subjects' facial skin and the baseline, transepidermal water losses from subjects' facial skin in Week 12 are alleviated by 18% (from the baseline (13.55 (±17.45)) to the mean in Week 12 (11.18 (±5.87)). Accordingly, the cosmetic composition in the present disclosure proves effectiveness in alleviating transepidermal water losses.

Embodiment 11: Increase of the Hyaluronic Acid Score Based on Live Skin Slices

In Embodiment 11, any changes in the hyaluronic acid score based on live skin slices of subjects in Week 12 relative to the baseline (data collected one week before the human clinic trial) are evaluated and taken as the major indicator of the curative effect.

The hyaluronic acid score is created according to test results of hyaluronic acid staining with which target cells stained by colloidal iron stains present Prussian blue that is considered as collections of hyaluronic acids, particularly more hyaluronic acids displayed by a thicker and more intensive blue color (equivalent to a higher hyaluronic acid score). FIG. 1 demonstrates the reference standard of hyaluronic acid score, for example, Score 3, Score 5 and Score 7. In Embodiment 11, the statistics for changes in the hyaluronic acid score collected from subjects in Week 12 relative to the baseline are shown in Table 12.

TABLE 12

|  | Hyaluronic acid score | | | | | | Mean hyaluronic acid score |
| --- | --- | --- | --- | --- | --- | --- | --- |
|  | 2 | 3 | 4 | 5 | 6 | 7 |  |
| Baseline (Case count) | 1 | 4 | 2 | 1 | 4 | 0 | 4.25 |
| Week 12 (Case count) | 0 | 0 | 2 | 4 | 3 | 3 | 5.58 |

As shown in Table 12, the mean hyaluronic acid score for live skin slices changes from 4.25 (baseline) to 5.58 (Week 12) that means the hyaluronic acid score increases by 31% after 12 weeks during which subjects applied the cosmetic product on their skin. Moreover, the significant difference for case counts between the baseline and Week 12 is observed through the Kruskal-Wallis Test (p-value= 0.033572).

Figure 2:
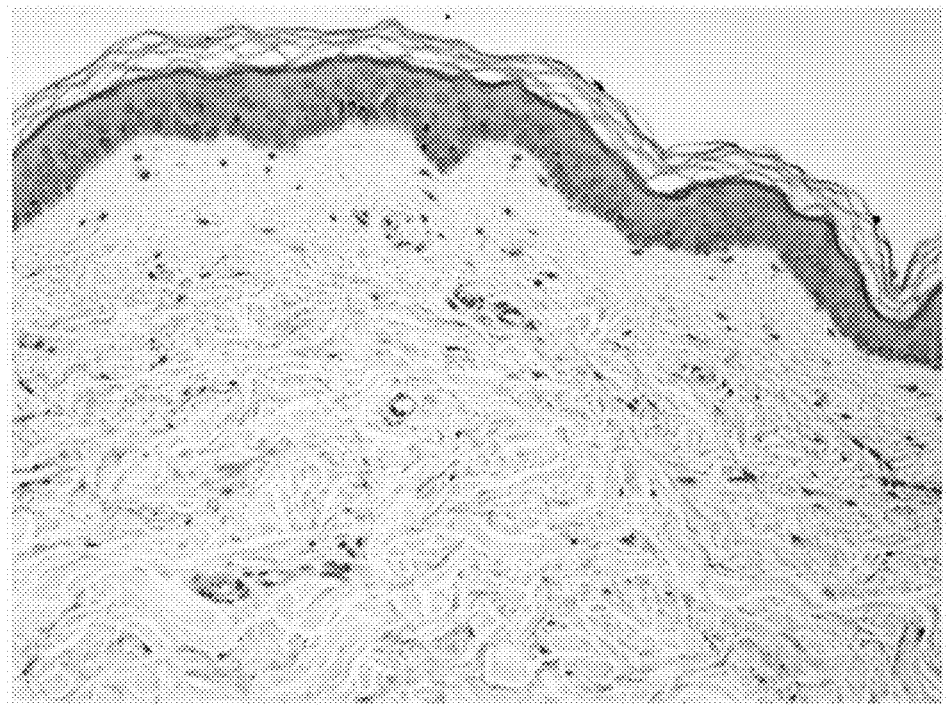
FIG. 2 demonstrates hyaluronic acid staining for a subject's skin specimen changing from the baseline to that on Week 12 in Embodiment 11.
Figure 2:
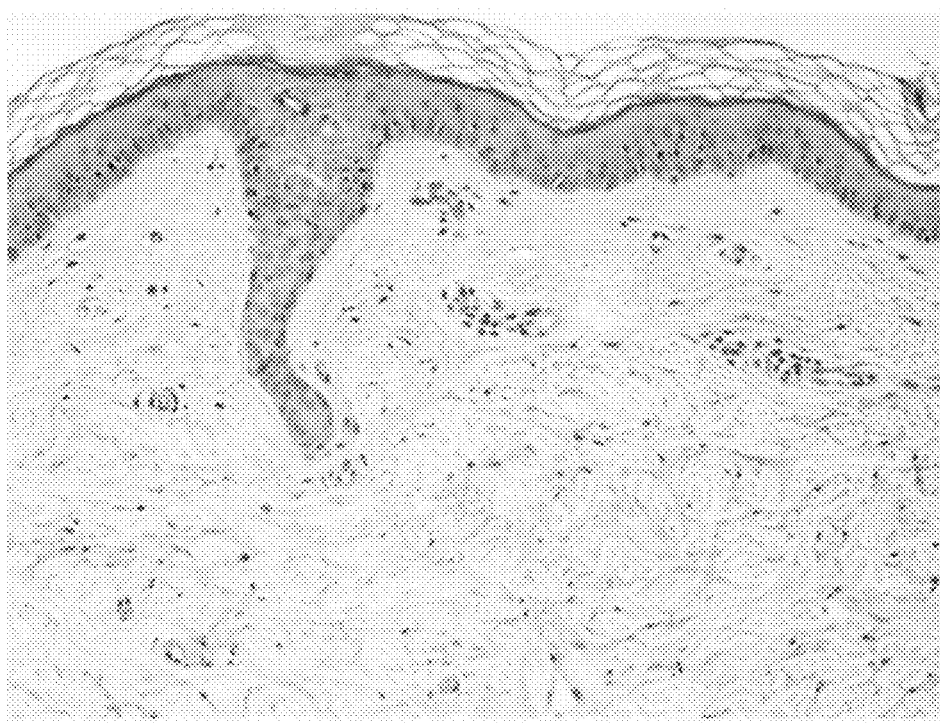

For example, the test result of hyaluronic acid staining for one subject in FIG. 2 indicates the hyaluronic acid score increases from 3 (baseline) to 7 (Week 12) and the blue color is thicker and more intensive. Accordingly, the cosmetic composition in the present disclosure proves effectiveness in increasing the hyaluronic acid score.

Embodiment 12: Increase of the Collagen Score Based on Live Skin Slices

In Embodiment 12, any changes in the collagen score based on live skin slices of subjects in Week 12 relative to the baseline (data collected one week before the human clinic trial) are evaluated and taken as the major indicator of the curative effect.

The collagen score is created according to test results of collagen staining with which stained target cells present a deep and intensive pigment that is granted a higher collagen score and considered as collections of more collagens. In Embodiment 12, two types of collagens, Type I collagen and Type III collagen, are checked and any changes in the collagen score in Week 12 relative to the baseline are compared. The statistics collected from subjects for Type I collagen are shown in Table 13.

TABLE 13

|  | Type I Collagen Score | | | | | Mean Type I Collagen Score |
| --- | --- | --- | --- | --- | --- | --- |
|  | 3 | 4 | 5 | 6 | 7 |  |
| Baseline (Case count) | 1 | 2 | 8 | 1 | 0 | 4.75 |
| Week 12 (Case count) | 0 | 1 | 6 | 4 | 1 | 5.42 |

As shown in Table 13, the mean Type I collagen score for live skin slices changes from 4.75 (baseline) to 5.42 (Week 12) that means the Type I collagen score increases by 15% after 12 weeks during which subjects applied the cosmetic product on their skin. Moreover, the significant difference for case counts between the baseline and Week 12 is observed through the Kruskal-Wallis Test (p-value=0.0313).

Figure 3:
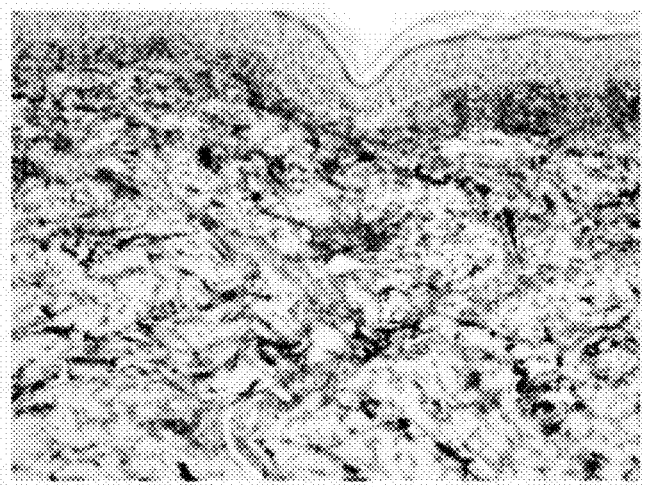
FIG. 3 demonstrates the reference standard of the Type III collagen score for Score 3, Score 5 and Score 7 in Embodiment 12.
Figure 3:
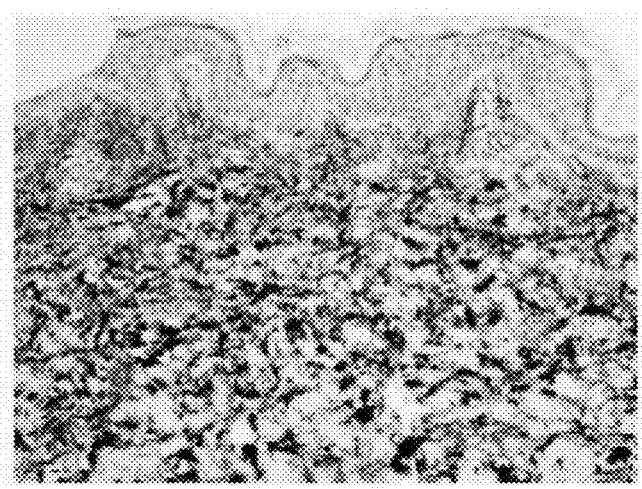
Figure 3:

FIG. 3 demonstrates the reference standard of the Type III collagen score, for example, Score 3, Score 5 and Score 7. The statistics collected from subjects for Type III collagen are shown in Table 14.

TABLE 14

|  | Type III Collagen Score | | | | Mean Type III Collagen Score |
| --- | --- | --- | --- | --- | --- |
|  | 4 | 5 | 6 | 7 |  |
| Baseline (Case count) | 5 | 5 | 2 | 0 | 4.75 |
| Week 12 (Case count) | 1 | 7 | 2 | 2 | 5.42 |

As shown in Table 14, the mean Type III collagen score for live skin slices changes from 4.75 (baseline) to 5.42 (Week 12) that means the Type III collagen score increases by 15% after 12 weeks during which subjects applied the cosmetic product on their skin. Moreover, the significant difference for case counts between the baseline and Week 12 is observed through the Kruskal-Wallis Test (p-value= 0.0156).

Figure 4:
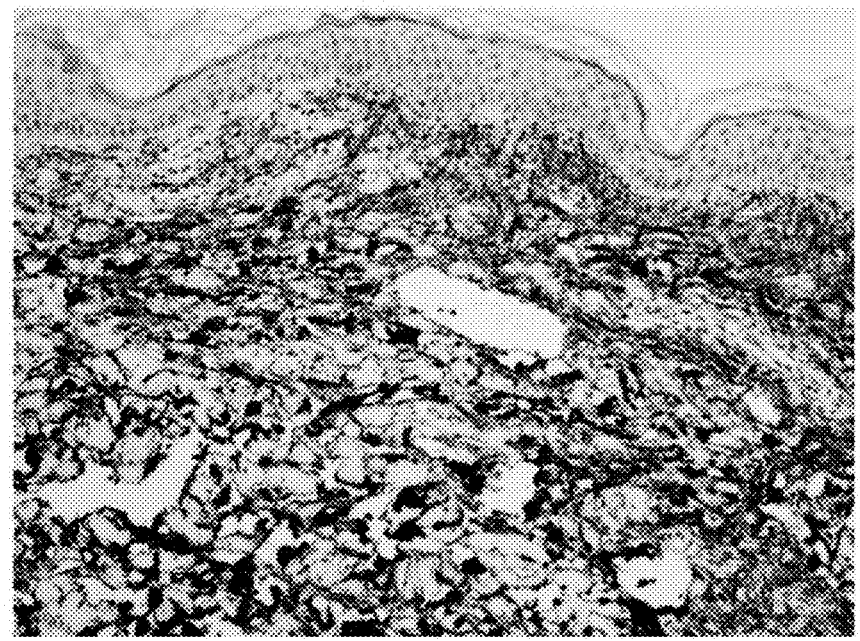
FIG. 4 demonstrates Type III collagen staining for a subject's skin specimen changing from the baseline to that on Week 12 in Embodiment 12.
Figure 4:
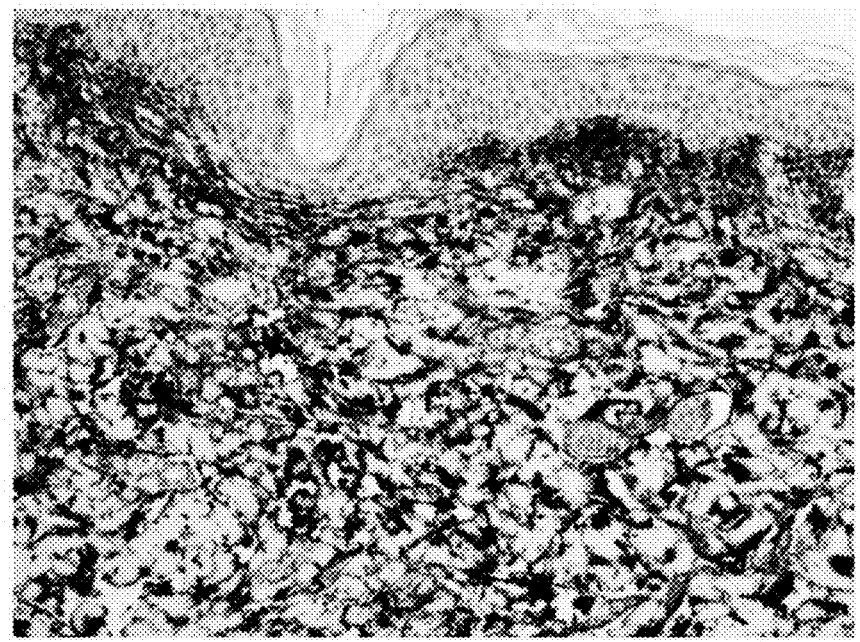

For example, the test result of Type III collagen staining for one subject in FIG. 4 indicates the collagen score increases from 5 (baseline) to 7 (Week 12). Accordingly, the cosmetic composition in the present disclosure proves effectiveness in increasing the collagen score.

Embodiment 13: Increase of the Elastic Fiber Score Based on Live Skin Slices

In Embodiment 13, any changes in the elastic fiber score based on live skin slices of subjects in Week 12 relative to the baseline (data collected one week before the human clinic trial) are evaluated and taken as the major indicator of the curative effect.

Figure 5:
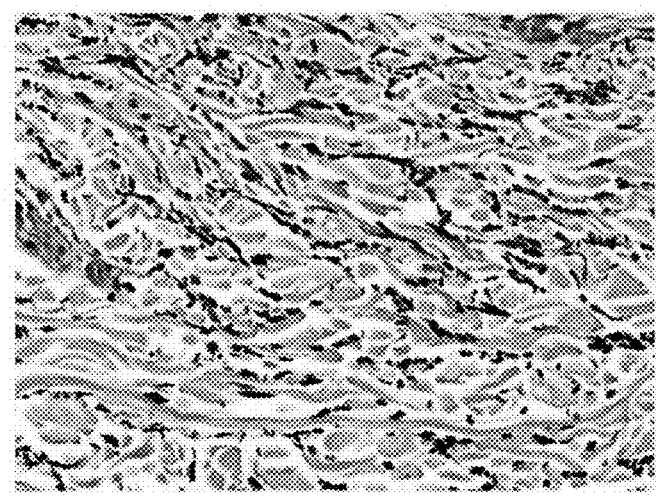
FIG. 5 demonstrates the reference standard of the elastic fiber score for Score 3, Score 5 and Score 7 in Embodiment 13.
Figure 5:
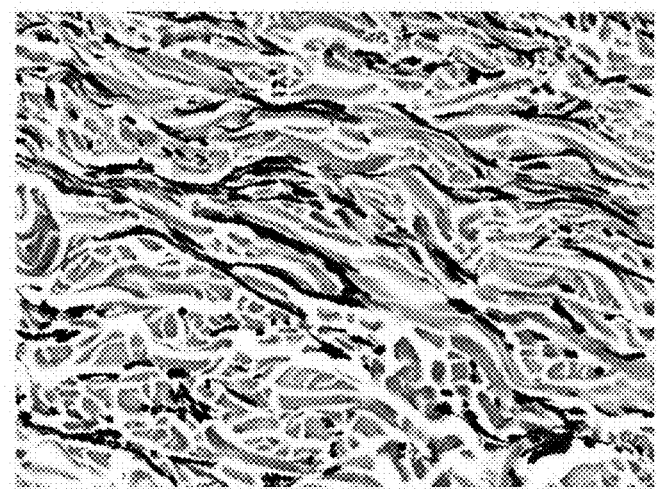
Figure 5:
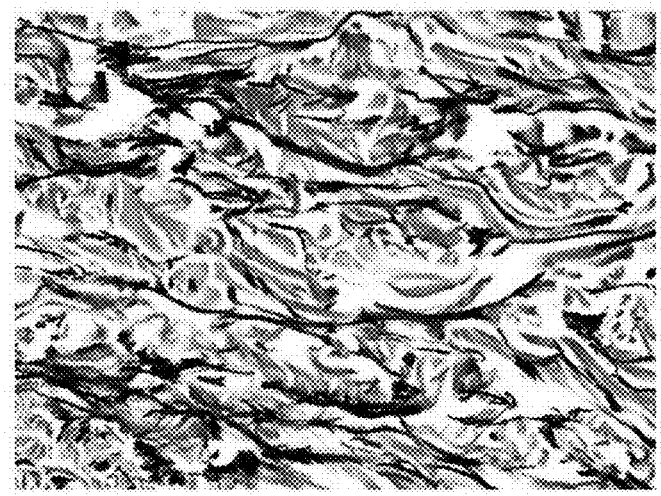

The staining status of elastic fiber debris attributed to skin photoaging is evaluated by the ranking score that represents different levels of elastic fiber debris. Moreover, elastic fibers vertically arranged between dermis and epidermis are the symbol of "younger skin" but rare in aging skin. FIG. 5 demonstrates the reference standard of the elastic fiber score, for example, Score 3, Score 5 and Score 7. In Embodiment 13, any changes in the elastic fiber score based on live skin slices of subjects in Week 12 relative to the baseline (data collected one week before the human clinic trial) are compared and statistics collected from subjects are shown in Table 15.

TABLE 15

|  | Elastic fiber score | | | | | | | Mean elastic fiber score |
| --- | --- | --- | --- | --- | --- | --- | --- | --- |
|  | 3.5 | 3.8 | 4 | 4.3 | 4.5 | 4.8 | 5 |  |
| Baseline (Case count) | 3 | 2 | 1 | 2 | 1 | 2 | 1 | 4.15 |
| Week 12 (Case count) | 0 | 0 | 2 | 1 | 2 | 3 | 4 | 4.65 |

As shown in Table 15, the mean elastic fiber score for live skin slices changes from 4.15 (baseline) to 4.65 (Week 12) that means the elastic fiber score increases by 12% after 12 weeks during which subjects applied the cosmetic product on their skin. Moreover, the significant difference for case counts between the baseline and Week 12 is observed through the Kruskal-Wallis Test (p-value=0.0029).

Figure 6:
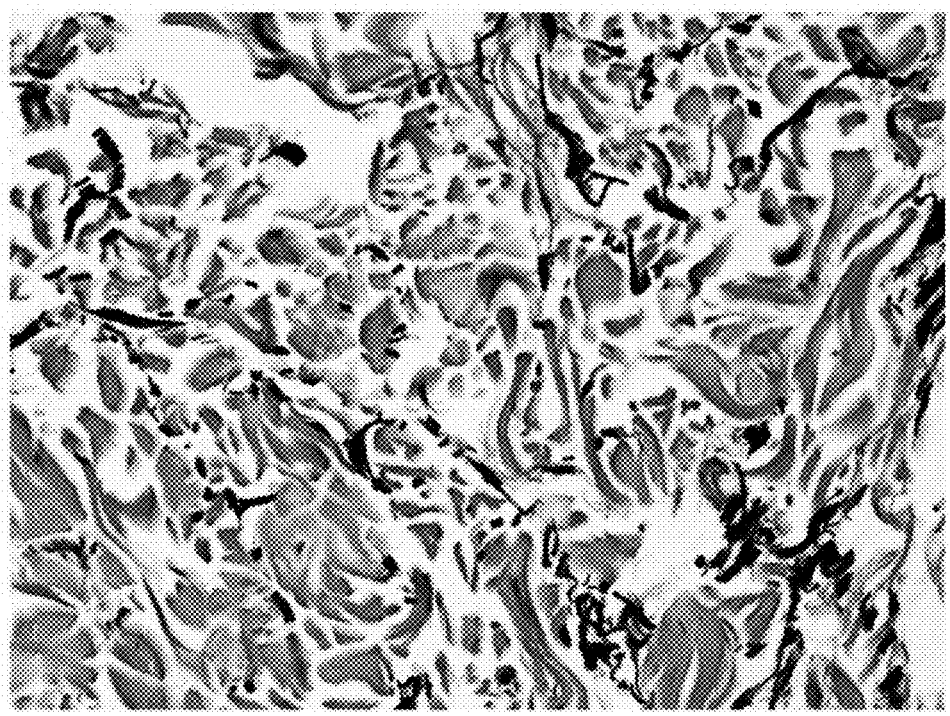
FIG. 6 demonstrates elastic fiber staining for a subject's skin specimen changing from the baseline to that on Week 12 in Embodiment 13.
Figure 6:
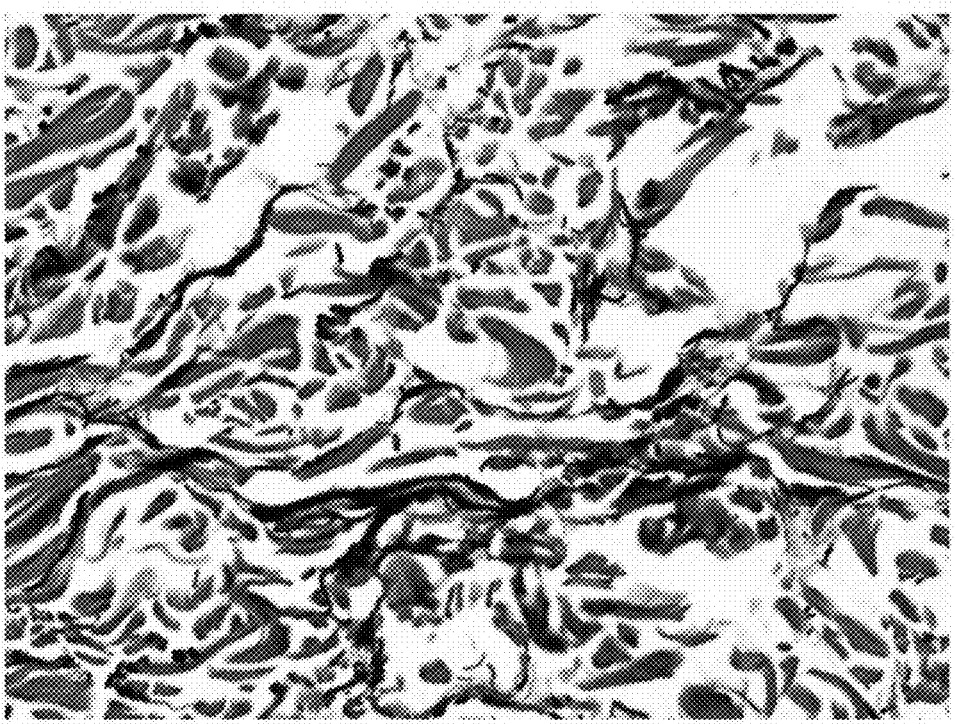

For example, the test result of elastic fiber staining for one subject in FIG. 6 indicates the elastic fiber score increases from 3 (baseline) to 7 (Week 12). Accordingly, the cosmetic composition in the present disclosure proves effectiveness in increasing the elastic fiber score.

Embodiment 14: Evaluation of Wrinkles by the VISIA Skin Analysis System

In Embodiment 14, any changes in facial wrinkles of subjects in Week 12 relative to the baseline (data collected one week before the human clinic trial) are evaluated and taken as the major indicator of the curative effect.

For example, alleviations of a subject's wrinkles on left and right faces are evaluated by the VISIA Skin Analysis System.

Figure 7:
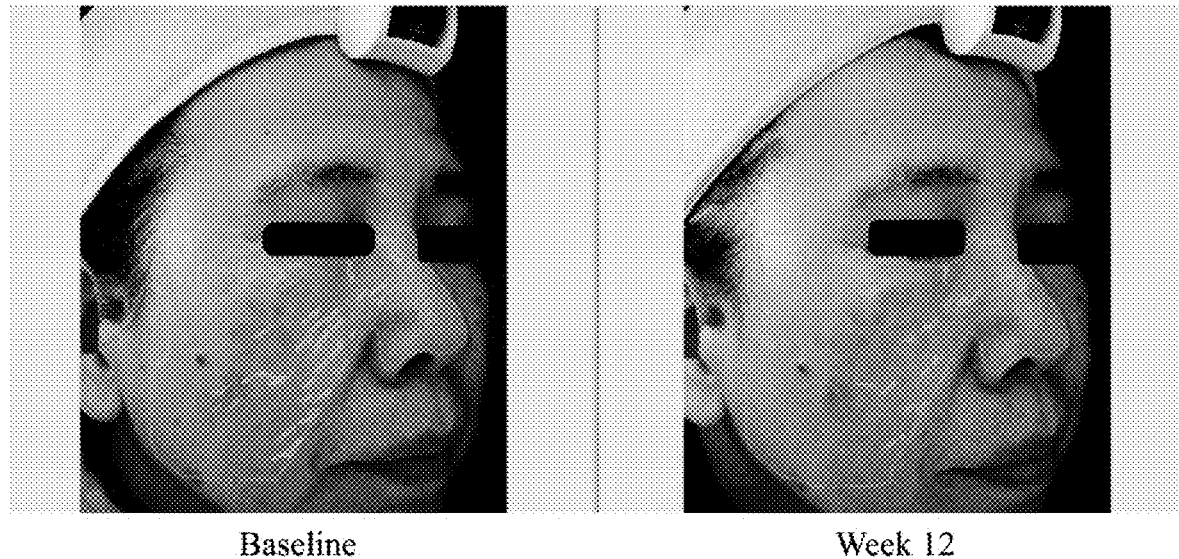
FIG. 7 demonstrates test results by the VISIA Skin Analysis System for a subject's wrinkles on the right face changing from the baseline to that on Week 12 in Embodiment 14.

As shown in FIG. 7, the percentile of the mean for the subject's wrinkles on the right face changes from 24% (baseline) to 43% (Week 12) that means wrinkles on the right face are improved by 79%. The test results are summarized in Table 16:

TABLE 16

|  | Feature count | Score | Percentile |
|---|---|---|---|
| Baseline | 45 | 10.645 | 24% |
| Week 12 | 22 | 7.464 | 43% |

Figure 8:
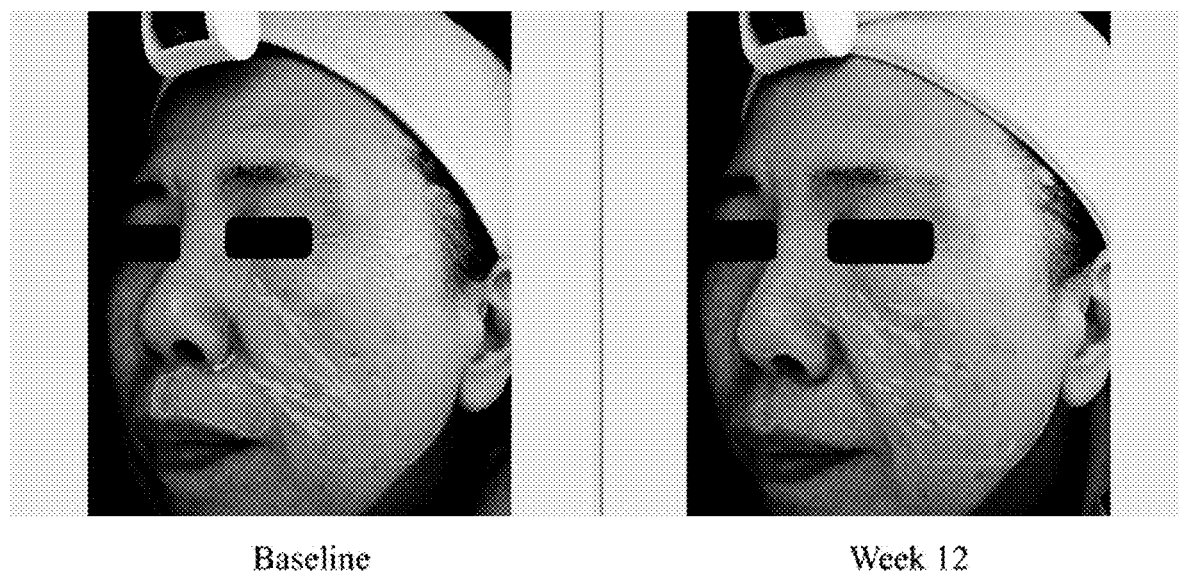
FIG. 8 demonstrates test results by the VISIA Skin Analysis System for a subject's wrinkles on the left face changing from the baseline to that on Week 12 in Embodiment 14.

As shown in FIG. 8, the percentile of the mean for the subject's wrinkles on the left face changes from 13% (baseline) to 49% (Week 12) that means wrinkles on the left face are improved by 277%. The test results as shown in Table 17:

TABLE 17

|  | Feature count | Score | Percentile |
|---|---|---|---|
| Baseline | 45 | 13.919 | 13% |
| Week 12 | 30 | 6.742 | 49% |

Accordingly, the cosmetic composition in the present disclosure proves effectiveness in smoothing away wrinkles.

Embodiment 15: Evaluation of Skin Textures by the VISIA Skin Analysis System In Embodiment 15, any changes in skin textures of subjects in Week 12 relative to the baseline (data collected one week before the human clinic trial) are evaluated by the VISIA Skin Analysis System and taken as the major indicator of the curative effect.

For example, alleviations of skin textures on a subject's left and right faces are evaluated by the VISIA Skin Analysis System.

Figure 9:
FIG. 9 demonstrates test results by the VISIA Skin Analysis System for a subject's skin textures on the right face changing from the baseline to that on Week 12 in Embodiment 15.

As shown in FIG. 9, the percentile of the mean for skin textures on the subject's right face changes from 81% (baseline) to 94% (Week 12) that means skin textures on the subject's right face are improved by 16%. The test results are summarized in Table 18:

TABLE 18

|  | Feature count | Score | Percentile |
|---|---|---|---|
| Baseline | 494 | 1.948 | 81% |
| Week 12 | 257 | 0.845 | 94% |

Figure 10:
FIG. 10 demonstrates test results by the VISIA Skin Analysis System for a subject's skin textures on the left face changing from the baseline to that on Week 12 in Embodiment 15.

As shown in FIG. 10, the percentile of the mean for skin textures on the subject's left face changes from 70% (baseline) to 89% (Week 12) that means skin textures on the subject's left face are improved by 27%. The test results are summarized in Table 19:

TABLE 19

|  | Feature count | Score | Percentile |
|---|---|---|---|
| Baseline | 934 | 3.433 | 70% |
| Week 12 | 433 | 1.464 | 89% |

Accordingly, the cosmetic composition in the present disclosure proves effective in smoothing away skin textures.

The present disclosure offers a method to prevent and/or ameliorate skin aging, in which the cosmetic composition with cyclic phosphatidic acid and citrus flavonoid is applied on skin to be cured transdermally or on local skin topically at room temperature, wherein: the citrus flavonoid is hesperidin and/or hesperetin; the skin includes normal skin and ageing skin; the skin aging is selected from a combination of wrinkles, fine lines, skin darkening, dehydration, absence of pigments and absence of skin elasticity.

In the present disclosure, the steps for the method for preventing and/or ameliorating skin aging include, without limitation, promoting moisture retention of stratum corneum, promoting skin elasticity, increasing presence or elasticity of collagens and elastins in fibroblasts, increasing transfers of fibroblasts, promoting anti-oxidation, increasing generation of hyaluronic acid, alleviating wrinkles and skin textures, moderating melanin, reducing skin oil and preventing transepidermal water losses.

In summary, the cosmetic composition applied on skin contributes to significantly increasing moisture retention of skin, moderating transepidermal water losses, sustaining the water content of skin, preventing skin from fast aging due to dehydration, decreasing skin oil inside skin, alleviating melanin and making skin delicate and compact. In addition, the cosmetic composition, which is favorable to syntheses of hyaluronic acid and collagen/elastic fiber fragments for revived elastic fibers/skin elasticity, further proves effectiveness in moderating wrinkles and skin textures in the clinic trial and consists of natural ingredients without side effects for practical effects and safety.

The descriptions presented in embodiments of the specification are only technical philosophy and characteristics of the present application that can be understood and practiced by a person skilled in the art; the embodiments which should not be taken as examples to limit claims thereinafter may be modified or changed by the person based on the disclosed embodiments in the present disclosure without departing from the spirit of claims.

A cosmetic composition to prevent and/or ameliorate skin aging and applications thereof in the present application for multiple effects meets novelty and non-obviousness for patentability.

What is claimed is:

1. A cosmetic composition for preventing and/or ameliorating skin aging, comprising (a) cyclic phosphatidic acid, (b) propylene or butylene glycol, (c) glycerin and (d) citrus flavonoid;

wherein the citrus flavonoid is hesperidin and/or hesperetin;

wherein the cyclic phosphatidic acid is represented by a structural formula (I):

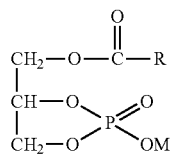 (I)

where R is linoleic acid, palmitic acid or oleic acid;
M is sodium (Na) or hydrogen (H); and
the molecular weight of the cyclic phosphatidic acid ranges from 300 to 500.

2. The cosmetic composition as claimed in claim 1, wherein the cyclic phosphatidic acid is sodium cyclic lyso-phosphatidic acid (NcPA).

3. The cosmetic composition as claimed in claim 1, wherein the cyclic phosphatidic acid features the weight percentage between 0.01% and 0.5%.

4. The cosmetic composition as claimed in claim 1, wherein the citrus flavonoid features the weight percentage between 0.01% and 0.5%.

5. The cosmetic composition as claimed in claim 1, wherein the cosmetic composition is in the form of an ointment, a lotion, a cream, a gel, liquid drops, a spray, a solution, a facial mask or an agent acceptable in pharmacy or cosmetology.

6. The cosmetic composition as claimed in claim 1, wherein the cosmetic composition further comprise moisturizing agents, surfactants, UV absorbents, fragrances, anti-oxidants, preservatives, body pigments, color pigments, pH adjusting agents, solvents or any other ingredients for general cosmetics or topical dermatologic drug compositions.

7. A method for preventing and/or ameliorating skin aging, in which a cosmetic composition is applied on skin to be cured transdermally or on local skin topically at room temperature, wherein the cosmetic composition comprising the composition of claim 1.

8. The method as claimed in claim 7, wherein the skin includes normal skin and aging skin.

9. The method as claimed in claim 7, wherein the skin aging is selected from a combination of wrinkles, fine lines, skin darkening, dehydration, absence of pigments and absence of skin elasticity.

10. The method as claimed in claim 7, wherein the preventing and/or ameliorating skin aging means promoting moisture retention of stratum corneum, promoting skin elasticity, increasing presence or elasticity of collagens and elastin in fibroblasts, increasing transfers of fibroblasts, promoting anti-oxidation, increasing generation of hyaluronic acid, alleviating wrinkles and skin textures, moderating melanin, reducing skin oil and preventing transepidermal water losses.

11. A method used for preventing and/or ameliorating skin aging, comprising topically or transdermally administering a composition of claim 1.

12. The cosmetic composition as claimed in claim 1, wherein the cyclic phosphatidic acid is a non-liposomal cyclic phosphatidic acid.

* * * * *